United States Patent [19]

Marin et al.

[11] Patent Number: 5,458,882
[45] Date of Patent: Oct. 17, 1995

[54] METHOD FOR REPELLING AEDES AEGYPTAE USING 3,7-DIMETHYL-6-OCTENENITRILE AND/OR 2(3,3-DIMETHYL-2-NORBORNYLIDENE)-ETHANOL-1

[75] Inventors: Anna B. Marin, Leonardo; Craig B. Warren, Rumson, both of N.J.; Jerry F. Butler, Gainesville, Fla.

[73] Assignees: International Flavors & Fragrances Inc., New York, N.Y.; The University Of Florida, Gainesville, Fla.

[21] Appl. No.: 157,403

[22] Filed: Nov. 26, 1993

[51] Int. Cl.⁶ .................................................. A01N 25/08
[52] U.S. Cl. .................... 424/411; 424/40; 424/403; 424/409; 424/405; 424/DIG. 10; 514/919
[58] Field of Search .................... 514/919, 729; 424/DIG. 10, 403, 405, 407, 409, 411, 40

[56] References Cited

U.S. PATENT DOCUMENTS

| | | | |
|---|---|---|---|
| 5,134,892 | 8/1992 | Wilson et al. | 73/866 |
| 5,165,926 | 11/1992 | Wilson et al. | 424/84 |
| 5,270,345 | 12/1993 | Coulston | 514/756 |

OTHER PUBLICATIONS

CA 119(5): 43293v Nomura et al. Synthesis of Physiologically Active Substances.
Nomura, et al, Nippon Nogei Kagaku Kaishi 1993, 67(4), pp. 693–700.

*Primary Examiner*—Thurman K. Page
*Assistant Examiner*—Neil Levy
*Attorney, Agent, or Firm*—Arthur L. Liberman

[57] ABSTRACT

Described is a method for repelling *Aedes aegyptae* comprising exposing a three dimensional space inhabitable by *Aedes aegyptae* to an *Aedes aegyptae*-repelling effective concentration and quantity of a composition of matter selected from the group consisting of:

(i) 3,7-DIMETHYL-6-OCTENENITRILE having the structure:

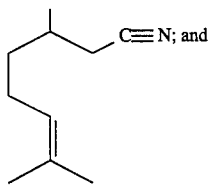

(ii) 2(3,3-DIMETHYL-2-NORBORNYLIDENE)ETHANOL-1 having the structure:

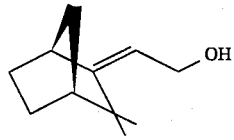

and insect repelling devices containing such compounds.

10 Claims, 4 Drawing Sheets

FIG.3-A
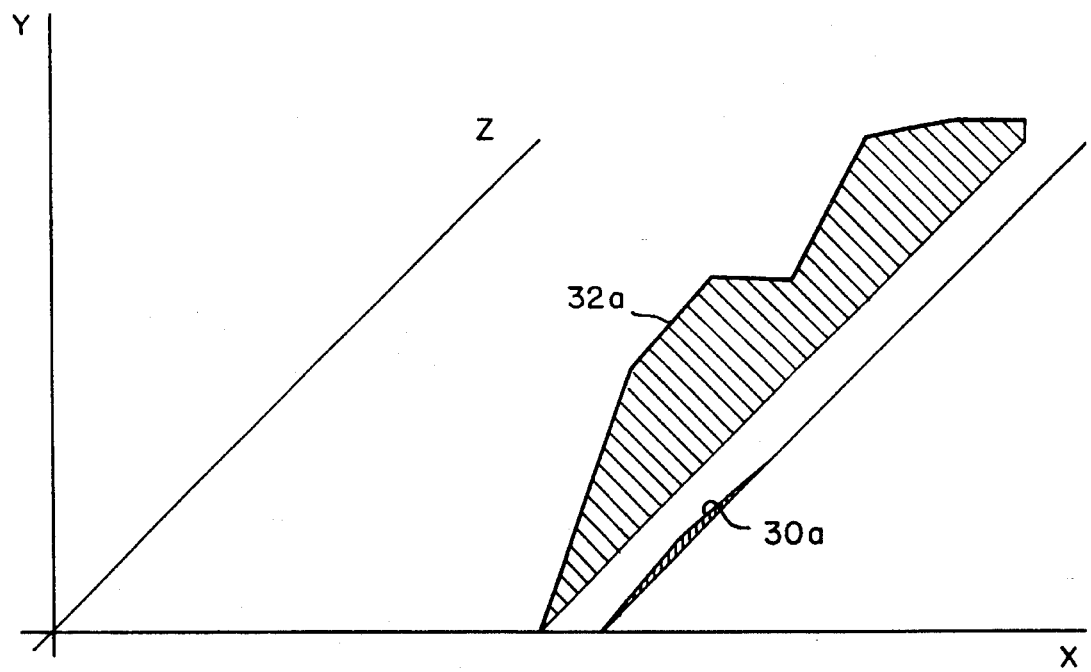
FIG.3-B
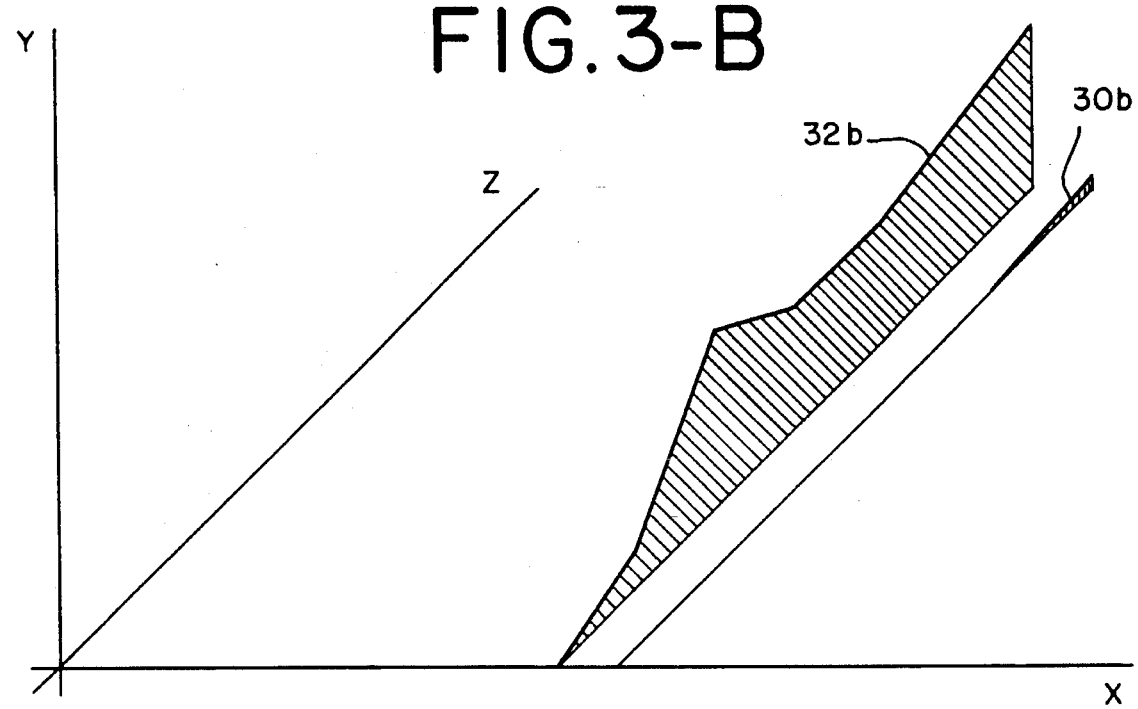

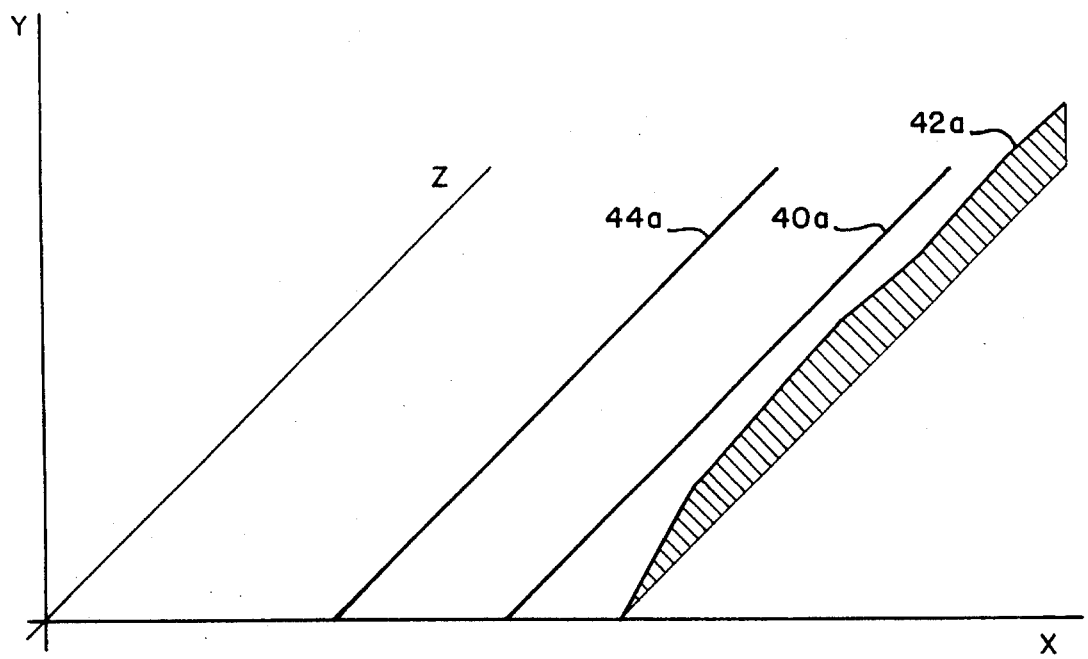
FIG.4-A
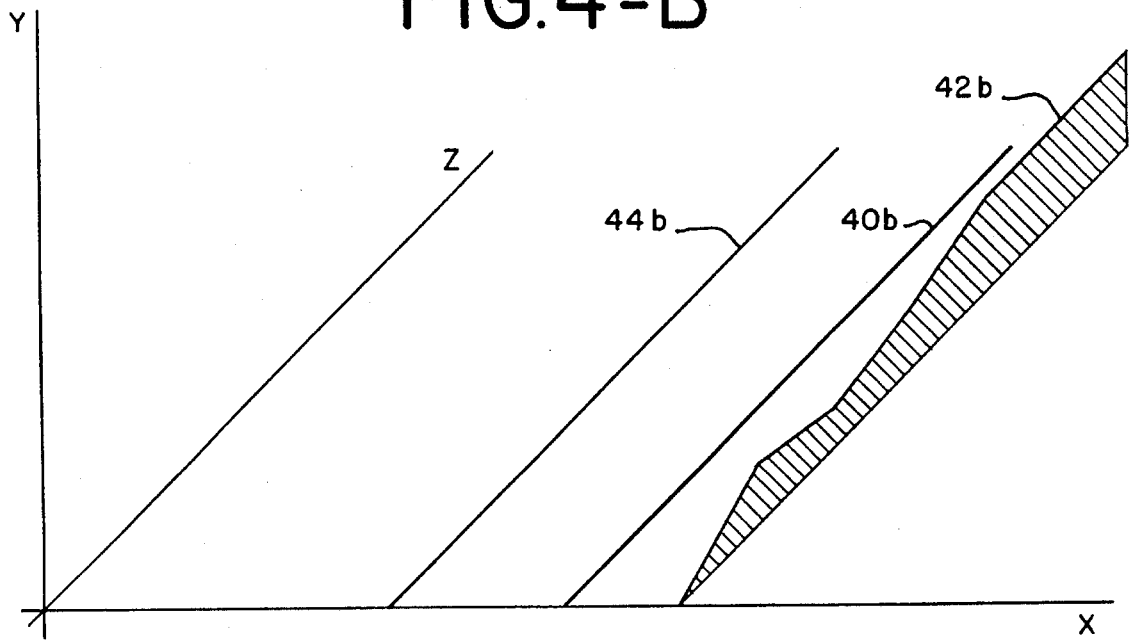
FIG.4-B

METHOD FOR REPELLING AEDES AEGYPTAE USING 3,7-DIMETHYL-6-OCTENENITRILE AND/OR 2(3,3-DIMETHYL-2-NORBORNYLIDENE)-ETHANOL-1

BACKGROUND OF THE INVENTION

This invention relates to the use of the nitrile having the structure:

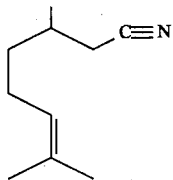

and the alcohol having the structure:

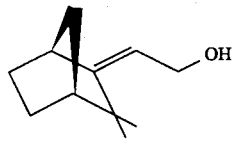

taken alone or in combination as repellents against the mosquito species, Aedes aegyptae.

A continuing need exists in the environment for repelling the mosquito species Aedes aegyptae from the proximity of mammalian species particularly in view of the fact that such insect species carry and transmit various diseases such as equine encephalitus.

A number of materials are well known in the art for repelling Aedes aegyptae including DEET®. However a need also arises for a repellent against Aedes aegyptae which is not only efficacious but is also aesthetically pleasing as an aroma.

The compound having the structure:

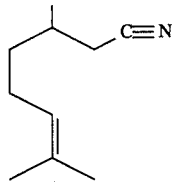

and the compound having the structure:

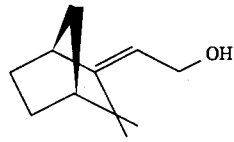

are efficacious Aedes aegyptae repellents and at the same time they have aesthetically pleasing aromas. Nothing in the prior art implies that compounds having such structures have the unobvious, advantageous, effectiveness against Aedes aegyptae that the compounds of our invention have.

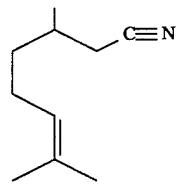

and the compound having the structure:

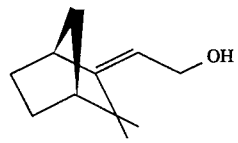

as repellents against the mosquito species Aedes aegyptae, indicating in schematic block flow diagram form the utilization of computer-assisted efficacy measuring apparatus; and also showing in block flow diagram form the interrelationship of the air and treatment agent mixing station with the entry ports for the resulting air treatment mixture into the olfactometer apparatus.

Figure 2:
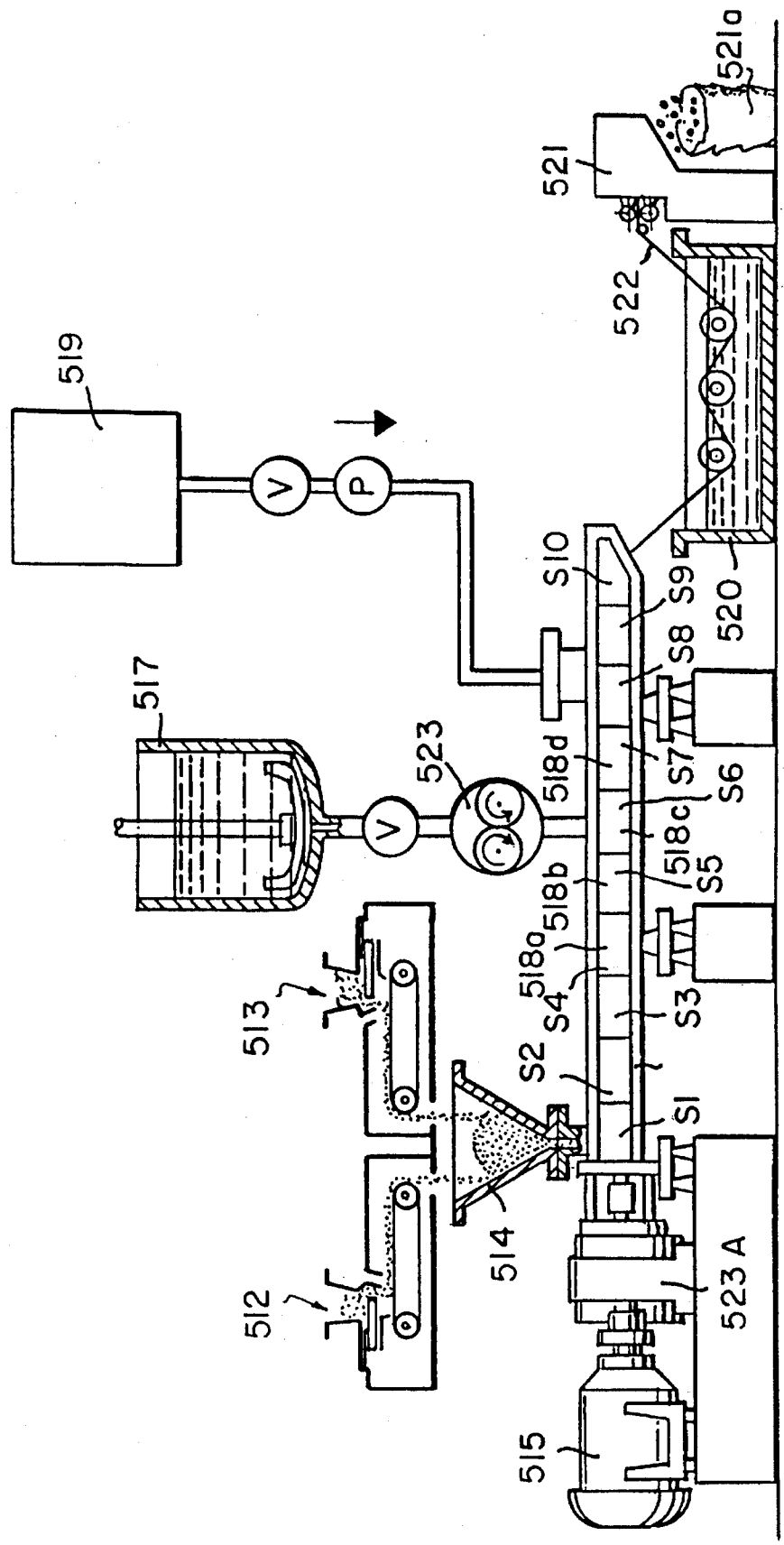

FIG. 2 is a cut-away side elevation schematic diagram of a screw extruder during the compounding of a resin with insect repellents including at least one of the compounds having the structure:

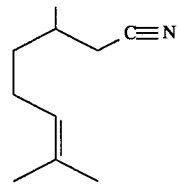

and/or having the structure:

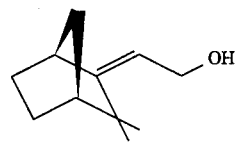

of our invention, while simultaneously adding foaming agent into the hollow portion of the barrel of the extruder and incorporates pelletizing apparatus used in pelletizing the extruded foamed tow product produced as a result of the extrusion operation.

FIG. 3A is a series of graphs depicted in three dimensions (in a rectangular mode for the "x" and "y" axes) showing the relative attractiveness or repellency for mosquitoes (Aedes aegyptae) of the compositions of matter:

(i) air; and (ii) the compound having the structure:

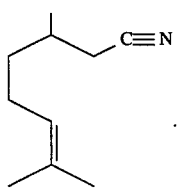

The graphs are based on experiments run for a total of 1 hour with six intervals of 10 minutes each. The results are tabulated in Table I(A), infra.

FIG. 3B is a series of graphs depicted in three dimensions (in a rectangular mode for the "x" and "y" axes) showing the relative attractiveness or repellency for mosquitoes (*Aedes aegyptae*) of the compositions of matter:

(i) air; and (ii) the compound having the structure:

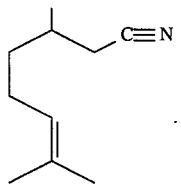

The graphs are based on experiments run for a total of 6 hours with six intervals of 1 hour each. The results are tabulated in Table I(B), infra.

FIG. 4A is a series of graphs depicted in three dimensions (in a rectangular mode for the "x" and "y" axes) showing the relative attractiveness or repellency for mosquitoes (*Aedes aegyptae*) of the compositions of matter:

(i) air;

(ii) a mixture of compounds containing 81 mole percent of geraniol having the structure:

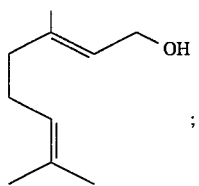

14 mole percent nerol having the structure:

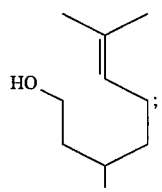

5 mole percent citronellol having the structure:

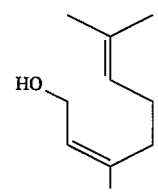

(iii) the compound having the structure:

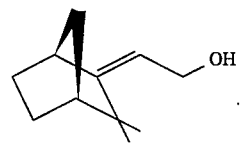

The graphs are based on experiments run for a total of 1 hour with six intervals of 10 minutes each. The results are tabulated in Table II(A), infra.

FIG. 4B is a series of graphs depicted in three dimensions (in a rectangular mode for the "x" and "y" axes) showing the relative attractiveness or repellency for mosquitoes (*Aedes aegyptae*) of the following compositions of matter:

(i) air;

(ii) a mixture of compounds containing 81 mole percent of geraniol having the structure:

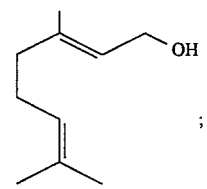

14 mole percent of nerol having the structure:

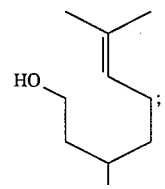

and 5 mole percent citronellol having the structure:

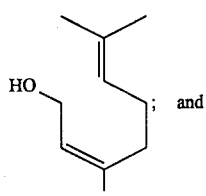

(iii) the compound having the structure:

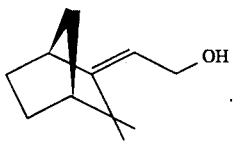

The graphs are based on experiments run for a total of 6 hours with six intervals of 1 hour each. The results are tabulated in Table II(B), infra.

THE INVENTION

The instant invention applies to the uses of the compounds having the structures:

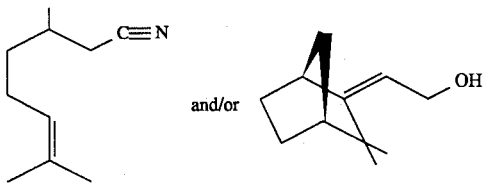

as repellents against the mosquito species *Aedes aegyptae*.

Our invention is also related to the use of the foregoing insect repellent compositions of matter in personal soap compositions, for example, the insect repellent soap composition described in U.S. Pat. No. 4,707,496 issued on Nov. 17, 1987, the specification for which is incorporated by reference herein. Thus, in applying the teachings of U.S. Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 to 7% by weight of a soap of caprylic acid, from 3.8 to 7% of a soap of capric acid, from 32.1 to 45% of a soap of lauric acid, from 12 to 17.5% by weight of a soap of myristic acid, from 5.0 up to 10% by weight of a soap of palmitic acid, from 1.6 to 3% by weight of a soap of stearic acid, from 3.5 to 5% by weight of a soap of oleic acid and from 0.9 to 5% by weight of a soap of linoleic acid;

(ii) from 0.1 up to 2% by weight of $C_8$–$C_{18}$ straight chain fatty acids;

(iii) from 10 up to 30% by weight of at least one of the repellent chemicals of our invention, e.g., the compound having the structure:

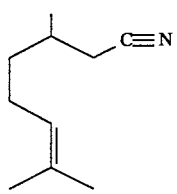

and/or the compound having the structure:

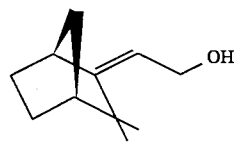

(iv) from 0.2 up to 5% by weight of an effective residual insecticide as described in U.S. Pat. No. 4,707,496.

Other insect repellent soaps can be produced by adding one or both of the compounds having the structures:

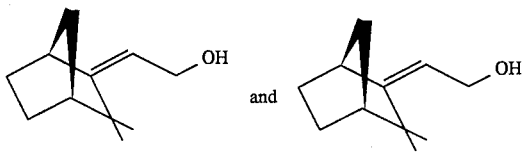

of our invention to one or more of the compositions described and claimed in U.S. Pat. No. 4,453,909 issued on Jun. 12, 1984 and U.S. Pat. No. 4,438,010 the specifications for which are incorporated by reference herein. Described in said U.S. Pat. No. 4,453,909 and U.S. Pat. No. 4,438,010 is a process for making a tablet of soap containing a perfume containing core, hollow, or solid fabricated from a hard plastic material either thermosetting or thermoplastic. The soap from the resulting composite tablet is useable until the core is washed clean and contains functional ingredients, e.g., the repellents described, supra, having the structures:

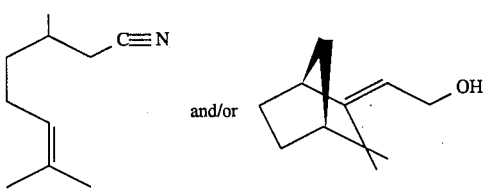

and optionally aromatizing agent (in addition to the repellents described above) until the core is washed clean. This obviates the wastage of soap which normally occurs as a conventional soap tablet becomes very thin on use and at the same time gives rise to a continuously functional ingredient-containing soap, (e.g., repellent and aromatizing) tablet. Thus, this invention also relates to detergent bars having a plastic core containing one or more of the above described compounds having the structure:

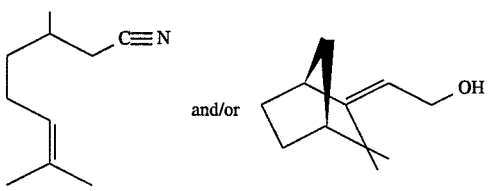

and optionally an additional perfuming material. More particularly, this invention relates to detergent bars intended for conventional toilet soap uses either as hand soaps or bath or shower soaps which are elastic or inelastic in nature but which contain a solid plastic core containing insect repellent and optionally perfume giving them unique properties which alleviate wastage thereof and causes the environment surrounding the soap on use thereof by an individual carrying out a washing procedure to be both insect repellent and aromatized in an aesthetically pleasing manner.

In addition, the compositions useful in repelling the *Aedes aegyptae* of our invention can also contain 1-nonen-3-ol described and claimed in U.S. Pat. Nos. 4,693,890 and 4,759,228 issued on Jul. 26, 1988, the specifications for which are incorporated by reference herein. The ratio of 1-nonen-3-ol:compound having the structure:

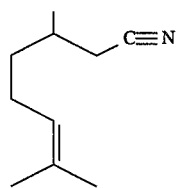

or compound having the structure:

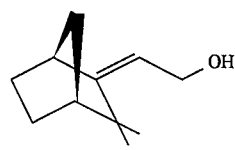

or both compounds of our invention useful in repellent compositions may vary from about 1 part 1-nonen-3-ol:99 parts alcohol or nitrile of our invention down to 99 parts 1-nonen-3-ol: 1 part nitrile or alcohol of our invention.

In addition to the soap fabrication, another aspect of our invention relates to the formation of repelling articles (that is, articles having the ability to repel *Aedes aegyptae* from a member of the mammalian species such as a person) containing one or both of the compounds having the structures:

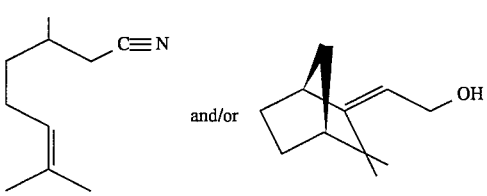

that is, articles useful for repelling the mosquito species *Aedes aegyptae* in combination with compatible polymers (e.g., high density polyethylene or low density polyethylene). Thus, another aspect of our invention provides a process for forming polymeric particles containing the compound having the structure:

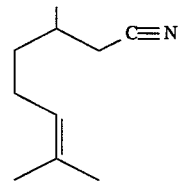

and/or compound having the structure:

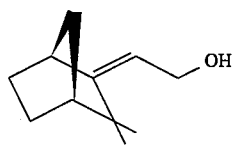

such as foamed polymeric particles which include a relatively high concentration of the compound having the structure:

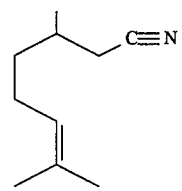

and/or the compound having the structure:

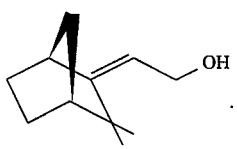

Thus, another aspect of our invention relates to the formation of polymeric pellets containing at least one of the compounds having the structure:

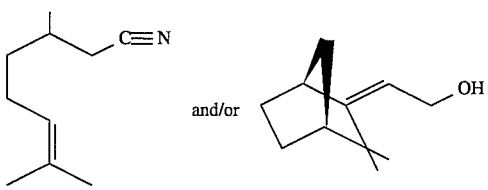

by means of introduction into a single screw or twin screw extruder of a polymer followed by at least one of the compounds having the structure:

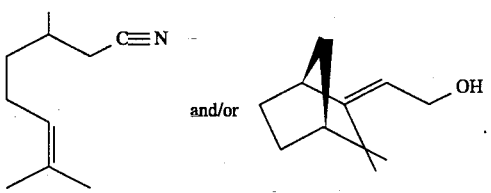

In turn, the introduction of such nitrile or alcohol may optionally be followed by introduction of a gaseous blowing agent or blowing agent which will produce a gas which is inert to the polymer and to the nitrile or alcohol of our invention previously introduced into the extruder.

The advantages of using a foamed polymeric particle and the details concerning the specific extruder and specific polymers so used are set forth at columns 30, 31, 32 and 33 of U.S. Pat. No. 5,165,926 issued on Nov. 24, 1992 the specification for which is incorporated by reference herein.

The feed rate range of the insect repellent composition containing at least one of the compounds having the structure:

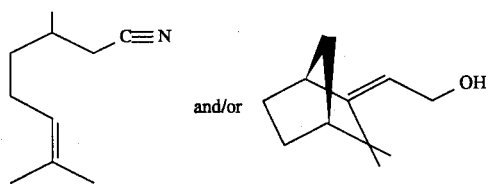

of our invention may be between about 0.5% up to about 45% by weight of the polymer.

In addition, our invention relates to candle body materials which on use are both insect repellent and perfuming which contain one or both of the compounds having the structures:

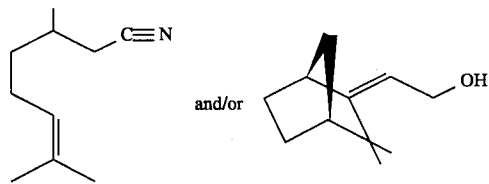

in order to repel the mosquito species *Aedes aegyptae*. The details concerning the formation of such candle compositions are set forth at columns 34, 35 and 36 of U.S. Pat. No. 5,165,926 issued on Nov. 24, 1992, the specification for which is incorporated by reference herein.

Specifically, the candle base composition can be standard paraffin wax or it can be transparent or pastel shade as more particularly described in U.S. Pat. No. 3,615,289 issued on Oct. 26, 1971 the disclosure of which is incorporated by reference herein and wherein the candle body comprises:

(i) a thermoplastic polyamide resin formed from linoleic acid polymerized with a polyamine compound;

(ii) an alkanol amide or alkanol amine; and (iii) a stearic acid compound.

The weight ratio of candle body:insect repellent-perfumant substance of our invention may vary from about 0.8% up to about 10% with a range of from about 0.8% up to about 2.0% being preferred when no additional perfume oil is used beyond the compounds having the structures:

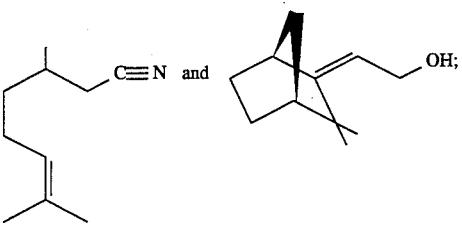

and with a range of from about 1.5% up to about 10% by weight of the overall composition being preferred when an additional perfume oil is used in conjunction with the compounds having the structures:

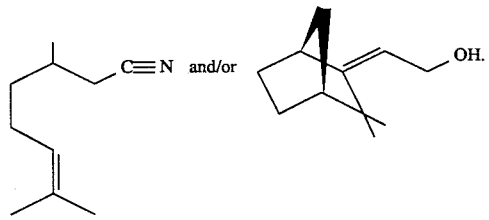

Specifically, the polyamide may be a "VERSAMID" resin which is a thermoplastic condensation product of polymerized linoleic acid with various polyamine compounds such as ethylene diamine, ethylene triamine and the like. Specific "VERSAMID" compounds are "VERSAMID® 900", "VERSAMID® 930", "VERSAMID® 940", "VERSAMID® 948", "VERSAMID® 950", and "VERSAMID® 1635". These compounds are products of the Henkel Chemical Corporation of Minneapolis, Minn.).

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as BARLOL®- 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready composition of the insect repellent/ perfumant compositions of our invention up to a level of approximately 5% (total proportion of perfume oil-insect repellent composition). They are carriers for the perfumant-insect repellent and may be used in a proportion of between 1 and 50% by weight of the composition although the preferable range is between 20 to 30%. In this connection it is possible to use up to about 10% by weight of a perfumant/ insect repellent if part of the formula is replaced by the material "NEVEX® 100", a product which is a coumarin-indene copolymer resin of very little unsaturation manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by referene herein. Such compositions of matter include:

(a) from about 35% up to about 85% by weight of an oil which is normally liquid at room temperature chosen from the group consisting of light mineral oils and natural oils having iodine values substantially within the range of 40–135;

(b) from about 7% up to about 40% by weight of a long chain polyamide having a molecular weight substantially within the range of 6000–9000 and a softening point substantially within the range of 18° C.–48° C.; and (c) from about 7% up to about 30% of an alcohol selected from the group consisting of 8 to 12 carbon primary alcohols.

DETAILED DESCRIPTION OF THE DRAWINGS

Figure 1:
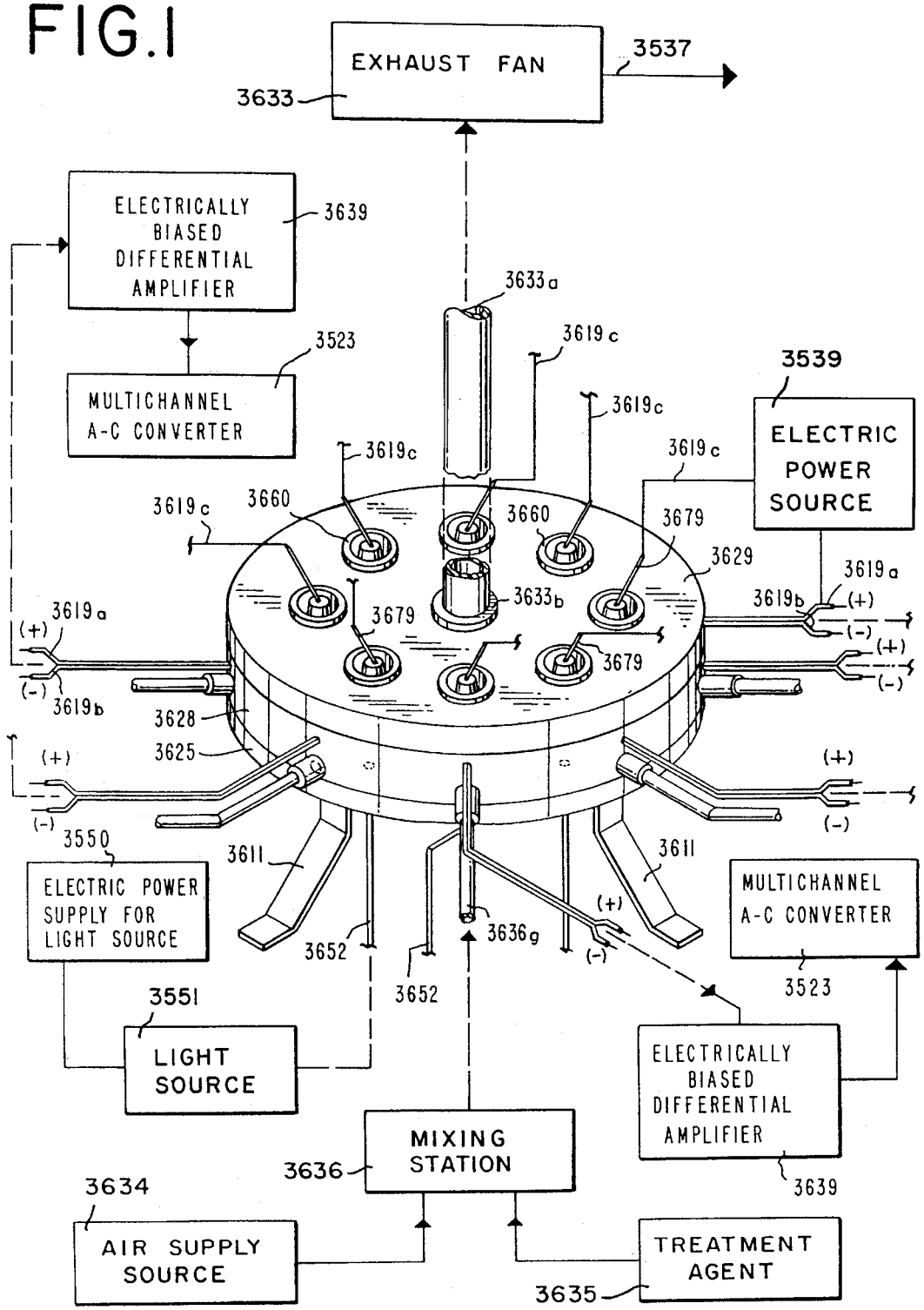
FIG. 1 is a schematic diagram of an embodiment of olfactometer apparatus useful in ascertaining the efficacy of such compounds as the compound having the structure.

FIG. 1 sets forth in perspective view an exploded view of an embodiment of the olfactometer apparatus used in testing the efficacy of the compounds having the structures:

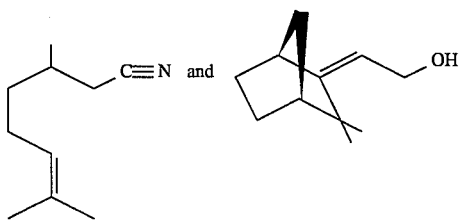

as mosquito (*Aedes aegyptae*) repelling materials.

Air supply source 3634 provides air to mixing station 3636 wherein the air is mixed with treatment agent from treatment agent source 3635 (source of, for example, the compound having the structure:

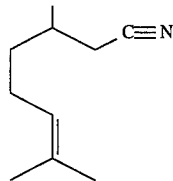

or the compound having the structure:

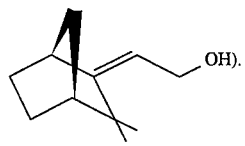

The resulting mixture passes through tube 3636g (for example) and enters the apparatus through side portals. The entry is through spacer plate 3628 and above base plate 3625. The entry of the air-treatment agent is in a direction parallel to the surface of the base plate 3625. Thus, the base plate 3625 is separated from the spacer plate 3629 for the air-treatment agent lines 3636g and 3636a. Air exits through line 3633a using exhaust fan 3633.

The air exits is indicated by reference numeral 3537.

Simultaneously, with the supplying of air and treatment agent from mixing station 3636, light is supplied from beneath the enclosed insect feeding and/or stimulating means collectively denoted as "IFS" means through light guides 3652, from light source 3551 which is powered by electric power supply 3550 marketed by RADIO SHACK®, Division of Tandy Corporation of Fort Worth, Tex. 76102 under the trademark ARCHER®, Catalog No. 276–228 ("1.0 mm optical plastic fiber length 5 meters"). An example of light source 3551 is KRATOS Monochromatic Illuminator GM 100 Miniature VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. The base plate 3625 is also separated from the spacer plate 3629 for the light guides 3652 whereby the light guides 3652 are held in place in the base plate 3625 whereby the light (or other forms of radiation) is directed in a direction perpendicular to the electric sensor element 3610. Air supply from source 3634 and treatment agent from location 3635 is mixed at mixing station 3636 where upon treatment agent and air in admixture is passed through lines 3636a and 3636g through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628.

The olfactometer operation is assisted with computer apparatus shown in schematic form and block flow diagram form in FIG. 1 using reference numerals 3520, 3521, 3523, and 3524 as well as 3639. Dampers 3611 hold base plate 3625 in place horizontally. When a mosquito (*Aedes aegyptae*) lands on the grid having wires 3699, the landing is recorded electrically through a sensor. The sensor causes an electric impulse caused by the pressure of the insects landing to proceed through wires 3619a and 3619b to an electrically biased differential amplifier 3639 (using electric power supply 3539 also connected to wire 3619c) which is connected to the electrode 3679 which is immersed in the feeding stimulant composition or stimulant for the insect and then to a multi-channel A.C. converter 3523. Converter 3523 is associated with program tape storage 3524, printer 3520 and data link to digital computer 3521.

FIG. 2 is a schematic cut-away elevation diagram of an extrusion and pelletizing apparatus useful in carrying out a process during the operation of the apparatus whereby the insect repellent having the structure:

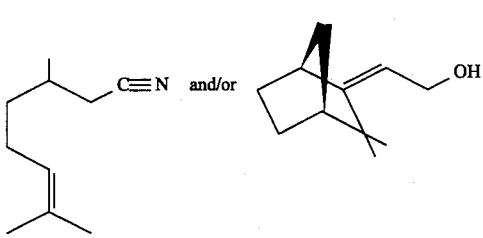

is incorporated into a polymer such as a polyethylene. Motor 515 drives the extruder screws located at 523A in barrel 516, the extruder being operated at temperatures in the range of about 150° C. up to about 250° C. At the beginning of the barrel resin at source 512 together with additives, e.g., processing aids and densifiers at location 513 is added via addition funnel 514 into the extruder. Simultaneously (when the operation reaches "steady state"), insect repellent, e.g., one of the compounds having the structure:

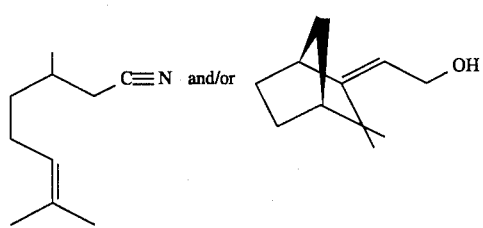

of our invention is added to the extruder at one or more barrel segments S-3, S-4, S-5, S-6, S-7 and S-8 of the extruder (which may be a twin screw or single screw extruder) at locations 518a, 518b, 518c and 518d (for example) by means of gear pump 523 from source 517. From source 519 into barrel segments S-5, S-6, S-7, S-8, S-9 and S-10 a gaseous or liquid blowing agent, e.g., nitrogen, carbon dioxide and the like as described, supra, are added simultaneously with the addition of insect repellent having one of the structures:

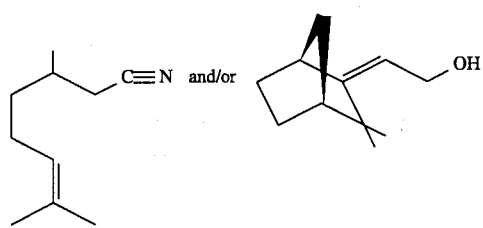

of our invention. The feed rate range of resin is about 80–300 pounds per hour. The feed rate range of the insect repellent compound having one of the structures:

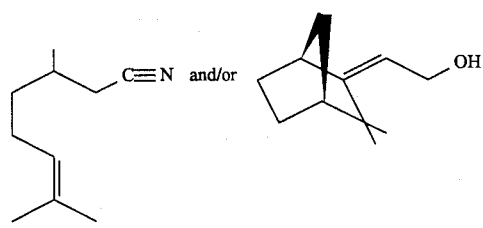

is between 1 and 35% of the feed rate range of the resin. The blowing agent range is such that the pressure of the gas or the pressure over the liquid being fed into the extruder is between about 50 and 200 psig if, indeed, a blowing agent is added. If desired the extruded ribbon or cylinder may be passed through water bath 520 and pelletizer 521 into collection apparatus 521a.

FIG. 3A is a series of graphs depicted in three dimensions (in a rectangular mode for the "x" and "y" axes) showing the relative attractiveness or repellency of the following compositions of matter:

(i) air; and (ii) the compound having the structure:

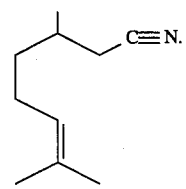

The graph indicated by reference numeral 32a is for air. The graph indicated by reference numeral 30a is for the compound having the structure:

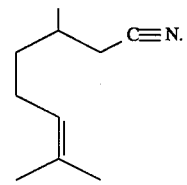

The graphs show the attractancy or repellency for mosquitoes (*Aedes aegyptae*) using the apparatus of FIG. 1. The graphs are based on experiments run for a total of 1 hour with six intervals of 10 minutes each. The results are tabulated in Table I(A) as follows:

TABLE I(A)

| Composition Tested | Graph No. | Insects Collected Per Interval | | | | | |
|---|---|---|---|---|---|---|---|
| The compound having the structure: ![C≡N] | 30a | 24 | 6 | 8 | 0 | 0 | 0 |
| Air | 32a | 478 | 513 | 277 | 466 | 277 | 53 |

FIG. 3B is a series of graphs depicted in three dimensions (in a rectangular mode for the "x" and "y" axes) showing the relative attractiveness or repellency of the following compositions of matter:

(i) air; and (ii) the compound having the structure:

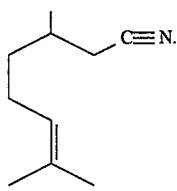

The graph indicated by reference numeral 30b is for the compound having the structure:

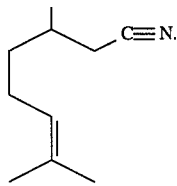

The graph indicated by reference numeral 32b is for air. The graphs show the attractancy or repellency for mosquitoes (*Aedes aegyptae*) using the apparatus of FIG. 1. The graphs are based on experiments run for a total of 6 hours with 6 intervals of 1 hour each. The results are tabulated in Table I(B) below:

TABLE I(B)

| Composition Tested | Graph No. | Insects Collected Per Interval | | | | | |
|---|---|---|---|---|---|---|---|
| The compound | 30b | 0 | 1 | 4 | 1 | 1 | 19 |
| The compound having the structure: | 30b | 0 | 1 | 4 | 1 | 1 | 19 |
| Air | 32b | 53 | 255 | 172 | 169 | 193 | 234 |

FIG. 4A is a series of graphs depicted in three dimensions (in a rectangular mode for the "x" and "y" axes) showing the relative attractiveness or repellency of several compositions of matter. The graph indicated by reference numeral 40a is for the compound having the structure:

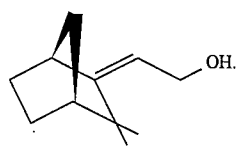

The graph indicated by reference numeral 42a is for air. The graph indicated by reference numeral 44a is for a mixture containing 81 mole percent geraniol having the structure:

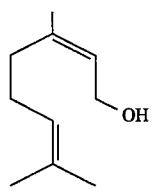

14 mole percent nerol having the structure:

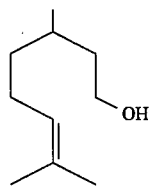

and 5 mole percent citronellol having the structure:

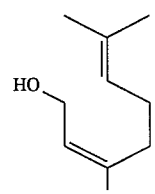

The graphs show the attractancy or repellency for mosquitoes (*Aedes aegyptae*) using the apparatus of FIG. 1. The graphs are based on experiments run for a total of 1 hour with six intervals of 10 minutes each. The results are tabulated in Table II(A) as follows:

TABLE II(A)

| Composition Tested | Graph No. | Insects Collected Per Interval | | | | | |
|---|---|---|---|---|---|---|---|
| The compound having the structure: 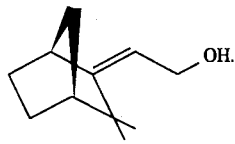 | 40a | 2 | 0 | 0 | 0 | 0 | 0 |
| Air | 42a | 173 | 184 | 205 | 186 | 201 | 183 |
| Mixture conaining 81 mole % geraniol; 14 mole % nerol; and 5 mole % citronellol | 44a | 0 | 0 | 0 | 0 | 0 | 0 |

FIG. 4B is a series of graphs depicted in three dimensions (in a rectangular mode for the "x" and "y" axes) showing the relative attractiveness or repellency of several compositions of matter. The graph indicated by reference numeral 40b is for the compound having the structure:

The graph indicated by reference numeral 42b is for air. The graph indicated by reference numeral 44b is for a mixture containing 81 mole percent geraniol, 14 mole percent nerol and 5 mole percent citronellol. The graphs show the attractancy or repellency for mosquitoes (*Aedes aegyptae*) using the apparatus of FIG. 1. The graphs are based on experiments run for a total of 6 hours with six intervals of 1 hour each. The results are tabulated in Table II(B) as follows:

TABLE II(B)

| Composition Tested | Graph No. | Insects Collected Per Interval | | | | | |
|---|---|---|---|---|---|---|---|
| The compound having the structure: | 40b | 0 | 0 | 0 | 0 | 0 | 0 |
| Air | 42b | 183 | 114 | 173 | 273 | 282 | 277 |
| Mixture containing 81 mole % geraniol; 14 mole % nerol; and 5 mole % citronellol | 44b | 0 | 0 | 0 | 0 | 0 | 0 |

The following examples illustrate the use of our insect repellents having the structures:

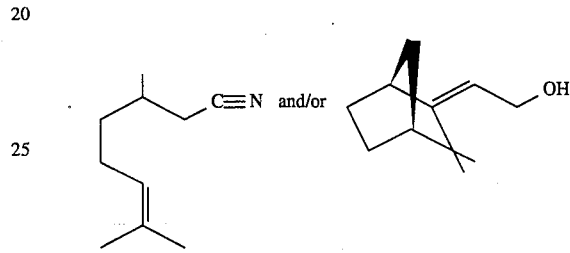

in candles. Our invention is not to be considered to be limited to these examples but is only limited by the claims following said examples.

EXAMPLE I

PARAFFIN WAX CANDLE BODY

The following composition is prepared:

| Ingredients | Parts by Weight |
|---|---|
| Paraffin Wax | 95.0 |
| 50:50 (Weight:weight) mixture of the compound having the structure: | |

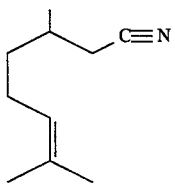

and the compound having the structure:                                            5.0

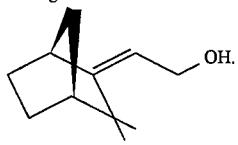

Paraffin wax is intimately admixed at 150° C. and 10 atmospheres pressure with the mixture of the compound having the structure:

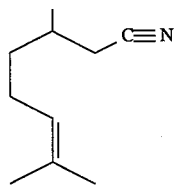

and the compound having the structure:

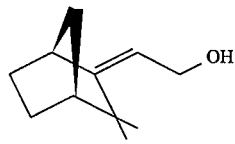

in an autoclave with intensive shaking. The autoclave pressure is maintained with a nitrogen atmosphere. At the end of the period of 1 hour the autoclave is depressurized, the autoclave is opened and the resulting mixture is poured into cylindrical candle molds containing wicks.

The resulting candles on use evolve an aesthetically pleasing aroma and, in addition, give rise to efficacious mosquito repellency (repellency against *Aedes aegyptae*). The candles are effective in preventing mosquitoes from entering a room in which one candle is burning for a period of 10 minutes, the said room having the dimensions of 6'×15'×15' having a 3'×3' open portal adjacent to a mosquito infested region (*Aedes aegyptae* infested region) in the month of August in the temperate zone (location: Highlands, N.J. next to Raritan Bay).

EXAMPLE II

A transparent candle base mixture is produced by intimately admixing the following ingredients:

| Ingredients | Parts by Weight |
| --- | --- |
| VERSAMID ®1635 | 34.0 |
| Barlol 12C2 | 51.0 |
| Butyl Stearate | 3.5 |
| NEVEX ®100 | 5.0 |
| SPAN ® | 1.5 |
| Isopropyl Isostearate | 4.0 |

-continued

| Ingredients | Parts by Weight |
| --- | --- |
| Isopropyl Myristate | 4.0. |

The foregoing mixture is placed in an autoclave and intimately admixed with a perfuming-insect repellent composition containing 5 parts by weight of the compound having the structure:

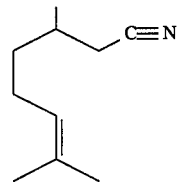

and 1 part by weight of the compound having the structure:

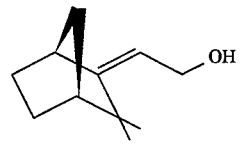

based on the total candle base composition.

The autoclave is sealed and heated to 180° C. under 15 atmospheres pressure and maintained with vigorous shaking for a period of 5 hours. At the end of the 5 hour period, the autoclave is depressurized (being a nitrogen pressure atmosphere) and the autoclave is opened and the contents are then poured into cylindrical candle molds 4" in height and 2" in diameter containing 0.125" wicks. The resulting candles have efficacious *Aedes aegyptae* repellencies and have aesthetically pleasing aromas on use.

The candles are effective in preventing *Aedes aegyptae* from entering a room in which two candles have been burning for 15 minutes, the said room having dimensions of 6'×15'×15' and having a 3'×3' open portal adjacent a *Aedes aegyptae*-infested region in the month of August, in the temperate zone of Highlands, N.J. adjacent Raritan Bay.

EXAMPLE III

The following candle base composition of matter is prepared:

| Ingredients | Parts by Weight |
| --- | --- |
| Polyamide (VERSAMID ® 940 manufactured by the Henkel Chemical Corporation of Minneapolis, Minnesota) | 30.0 |
| Stearic acid | 5.0 |
| Methyl-12-hydroxy stearate | 5.0 |
| 10 Carbon primary alcohol (Continental Oil Company ALFOL ® 10) (ALFOL ® is a trademark of Conoco Division of E. I. DuPont of Wilmington Delaware) | 5.0 |
| Myristyl Myristate | 10.0 |
| Stearic hydrazide | 0.1 |
| The compound having the structure: | 1.0 |

| Ingredients | Parts by Weight |
|---|---|
| 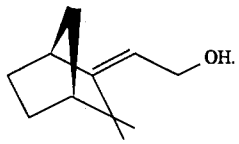 | |
| Light white mineral oil q.s. to | 100% |

All of the materials except the polyamide are mixed at room temperature. The mixture is then heated gradually with gradual addition of the polyamide and with agitation beginning with the commencement of addition of the polyamide. In the proportion required, the polyamide does not become fully soluble until the mixture reaches the temperature of about 220° F. The temperature on the order of 220° F. to 230° F. is maintained at atmospheric pressure with continued agitation until the polyamide is fully dissolved. Since higher temperatures promote solution of the polyamide this temperature range can be slightly exceeded with some advantages.

As soon as the polyamide has dissolved completely, the mixture is poured into molds following the conventional practice in the manufacture of molded candles. As the candles cool they harden. The candles are then freed from the molds and tested for *Aedes aegyptae* repellency.

The candles are effective in preventing *Aedes aegyptae* from entering a room in which two candles have been burning for 15 minutes, and said room having dimensions of 6'×15'×15' and having a 3'×3' open portal adjacent to an *Aedes aegyptae*-infested swamp region in the month of August in the temperate zone of Highlands, N.J. adjacent Raritan Bay.

What is claimed is:

1. A method for repelling *Aedes aegyptae* comprising the step of exposing a three dimensional space inhabitable by *Aedes aegyptae* to an *Aedes aegyptae*-repelling effective concentration and quantity of a composition of matter selected from the group consisting of:

(i) the 6-octenenitrile having the structure:

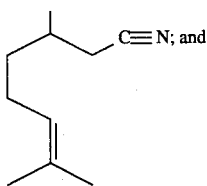

(ii) the 2-norbornylidene-ethanol-1 having the structure:

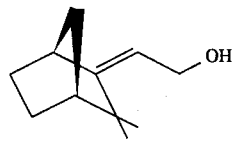

wherein said 6-octenenitrile and/or said 2-norbornylidene-ethanol-1:

(a) is present in a microporous polymer at the level of from about 0.5% up to about 45% by weight of the polymer;

(b) is present in the candle body of a burning candle in an amount of from about 0.8% up to about 2.0%; or (c) is present in a soap being applied in use in an amount of from 10 up to 30% by weight of the soap.

2. The process of claim 1 wherein the 6-octenenitrile and/or the 2-norbornylidene-ethanol-1 is present in a microporous polymer in an amount of from about 0.5% up to about 45% by weight of the polymer.

3. The process of claim 1 wherein the 6-octenenitrile and/or the 2-norbornylidene-ethanol-1 is present in a burning candle in an amount of from about 0.8% up to about 2.0% by weight of the candle composition.

4. The process of claim 1 wherein the 6-octenenitrile and/or the 2-norbornylidene-ethanol-1 is present in a soap-in-use in an amount of from 10% up to 30% by weight of the soap-in-use.

5. The process of claim 1 wherein the 6-octenenitrile and/or the 2-norbornylidene-ethanol-1 is embedded in a microporous polymer selected from the group consisting of copolymers of ethylene and a vinyl monomer selected from the group consisting of:

(a) vinyl acetate;
   (b) ethyl acrylate;
   (c) methyl acrylate;
   (d) butyl acrylate; and
   (e) acrylic acid and the hydrolyzed copolymer of ethylene and vinyl acetate compatible with both the 6-octenenitrile and the 2-norbornylidene-ethanol-1.

6. An insect repellent device consisting essentially of an insect repelling quantity of at least one compound selected from the group consisting of:

(i) the 6-octenenitrile having the structure:

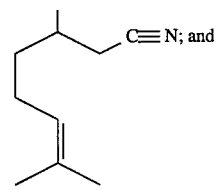

(ii) the 2-norbornylidene-ethanol-1 having the structure:

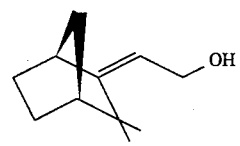

wherein the device is a candle consisting of a wick surrounded by a molded candle base mixture and wherein the 6-octenenitrile and/or the 2-norbornylidene-ethanol-1 is admixed with said candle base mixture in an amount of from 0.8 up to 2% by weight of the 6-octenenitrile and/or the 2-norbornylidene-ethanol-1.

7. The method of claim 1 wherein the repelling composition of matter has the structure:

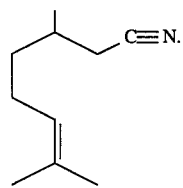
8. The method of claim 1 wherein the repelling composition of matter has the structure:
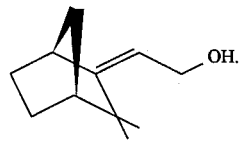
9. The insect repellent device of claim 6 wherein the repelling composition of matter has the structure:
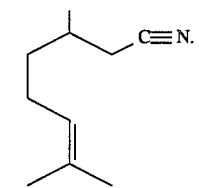
10. The insect repellent device of claim 6 wherein the repelling composition of matter has the structure:
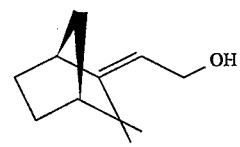
* * * * *